United States Patent [19]

Mårtensson

[11] Patent Number: 4,576,792
[45] Date of Patent: Mar. 18, 1986

[54] METHOD FOR HEAT TREATMENT OF ARTICLES AND ARRANGEMENT FOR CARRYING OUT THE METHOD

[75] Inventor: Karl I. M. Mårtensson, Slöinge, Sweden

[73] Assignee: Aktiebolaget Electrolux, Stockholm, Sweden

[21] Appl. No.: 650,847

[22] Filed: Sep. 17, 1984

[30] Foreign Application Priority Data

Sep. 23, 1983 [SE] Sweden .......................... 8305139

[51] Int. Cl.⁴ ............................................ A61L 2/08
[52] U.S. Cl. ........................................ 422/27; 422/26; 422/109; 422/116; 422/295; 134/36; 134/96; 134/102
[58] Field of Search .................. 422/26, 27, 295, 109, 422/116; 134/36, 96, 102

[56] References Cited

U.S. PATENT DOCUMENTS

| | | | |
|---|---|---|---|
| 4,192,845 | 3/1980 | Kalasek | 422/116 X |
| 4,225,555 | 9/1980 | Fahlvik | 422/26 X |
| 4,261,950 | 4/1981 | Bainbridge et al. | 422/27 X |
| 4,447,399 | 5/1984 | Runnells et al. | 422/27 X |

FOREIGN PATENT DOCUMENTS

| | | | |
|---|---|---|---|
| 909433 | 10/1962 | United Kingdom | 422/116 |
| 1575522 | 9/1980 | United Kingdom | 422/26 |

Primary Examiner—Arthur Kellogg
Attorney, Agent, or Firm—Alfred E. Miller

[57] ABSTRACT

In a chamber (24) in a pressure vessel, e.g. an autoclave (10), articles (26) are heat-treated by water, which is sprayed over the articles through nozzles (20) and supplies heat to or removes heat from the articles. Simultaneously, a gaseous medium, e.g. a mixture of steam and air, is forced by an impeller (34) to flow through the articles in countercurrent to the water. By this a very even temperature distribution of the articles in the chamber (24) is obtained.

7 Claims, 1 Drawing Figure

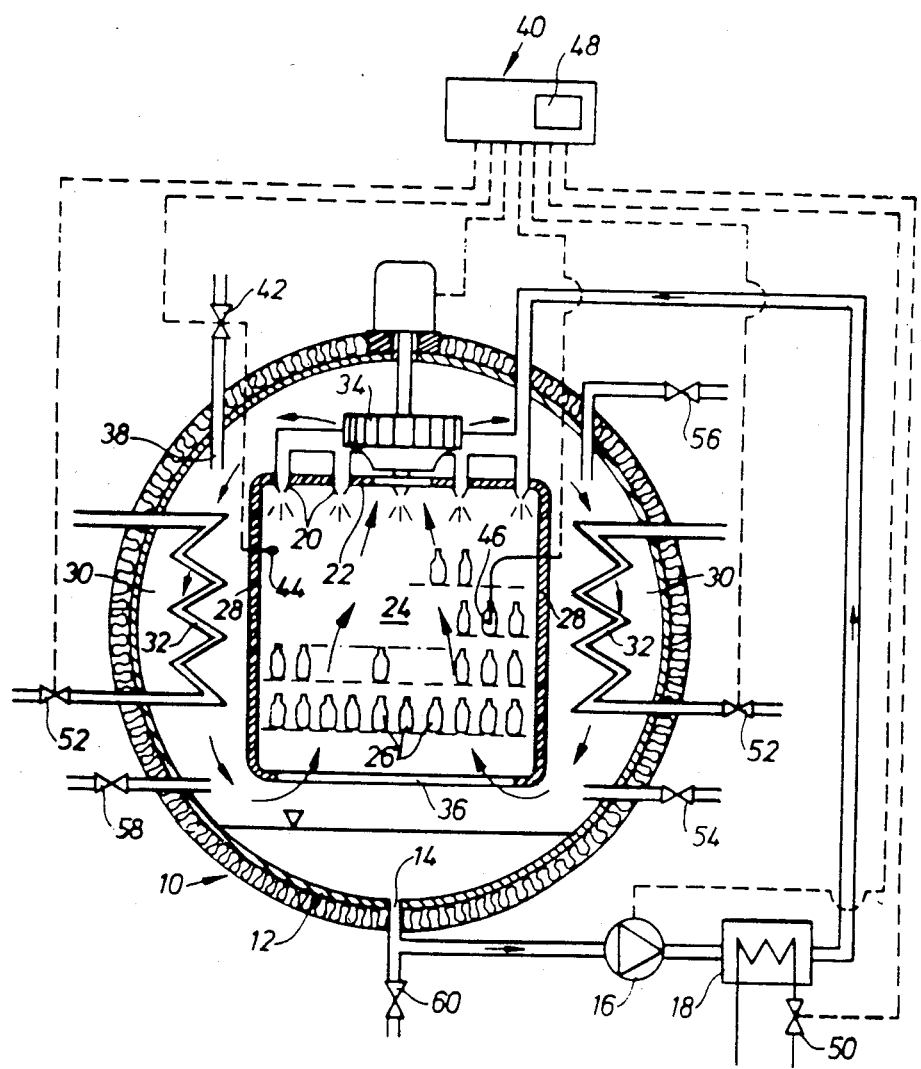

METHOD FOR HEAT TREATMENT OF ARTICLES AND ARRANGEMENT FOR CARRYING OUT THE METHOD

The present invention relates to a method for heat treatment of articles which are placed in a chamber in a pressure vessel, heat being supplied to and heat being removed from, respectively, the articles via water circulated in a closed circulation circuit and sprayed over the articles, which water during a heating period is heated by steam being introduced into the vessel and during a cooling period cooled by a first heat exchanger in the circulation circuit.

The invention furthermore relates to an arrangement for heat treatment of articles which are placed in a chamber in a pressure vessel for carrying out the method, which arrangement comprises a closed circulation circuit for water including a bottom outlet in the pressure vessel, a pump, a first heat exchanger and nozzles which spray the water over the articles in the chamber, and means for supplying steam to the vessel.

It is known to sterilize articles, e.g. liquids in glass- or plastic packages, in a pressure vessel. The packages are placed in the vessel, which is then closed, and the articles are heated to sterilizing temperature by water being sprayed through nozzles over the articles. This water is collected at the bottom of the vessel and pumped through a return conduit back to the nozzles. The water is heated by steam supplied to the vessel. When the sterilizing temperature has been reached and the articles have been kept at this temperature a certain time, the articles are cooled by water, which has been cooled in a heat exchanger in the return conduit, being sprayed over the articles. After that the vessel is opened and the sterilized articles can be taken out.

The drawback of the known method is that the articles in different parts of the vessel are unevenly heated and cooled, respectively, which is detrimental to the sterilizing result.

It is also known to sterilize articles, e.g. liquids in glass- or plastic packages, by exposing them to a flow of gaseous medium, which flow is generated by an impeller inside the pressure vessel. The gaseous medium can for example be composed by a mixture of air and steam. During heating steam is supplied to the vessel and circulated together with the air through the articles by the impeller. Inside the vessel a heat exchanger is arranged in the flow of gaseous medium to cool the gaseous medium during cooling of the articles.

This method also has the drawback, that articles in different parts of the vessel are unevenly heated and cooled, respectively.

The object of the invention is to eliminate said drawback and provide a temperature distribution of the articles in the chamber which is as even as possible. This object is attained by the method according to the invention thereby that simultaneously as the water is sprayed over the articles and flows downwards through them gaseous medium in the vessel is forced to flow upwards through the articles, and by the arrangement according to the invention thereby that an impeller is arranged in the vessel for generating a force circulating flow of gaseous medium through the articles in countercurrent to the water flowing downwards through the articles and that means are arranged for driving the impeller and the pump simultaneously.

An embodiment of an arrangement according to the invention will be described below with reference to the accompanying drawing. The drawing FIGURE is a cross sectional view of a pressure vessel filled with articles to be heat-treated and having means for controlling the process.

The numeral 10 designates a pressure vessel in the form of an insulated cylinder 12 with end walls (not shown). In the lower part of the vessel is an outlet 14, which communicates with a pump 16. The pressure side of the pump is connected to the inlet of a heat exchanger 18, the outlet of which is connected to several spray nozzles 20 positioned in the top wall 22 of a chamber 24, into which the articles to be sterilized, e.g. glass packages 26, are inserted. By the chamber 24 comprising vertical walls 28, the vessel obtains double-walled form. Heat exchangers 32 are arranged in ducts 30 located outside the walls 28.

In the upper part of the vessel there is an impeller 34, the inlet of which is located in the top wall 22 of the chamber 24. The outlet of the impeller is directed radially and communicates with the chamber via the ducts 30 and an opening 36 in the bottom of the chamber 24. In the vessel there are furthermore one or more steam inlets 38.

The arrangement works in the following way. After the articles to be heat-treated have been inserted into the chamber 24, the door (not shown) of the vessel is closed. A quantity of water is supplied to the lower part of the vessel via a valve 58. The treatment is thereafter started by a control means 40, which simultaneously starts the pump 16, so that water will be sprayed over the articles, the impeller 34, so that gaseous medium, at the beginning only air, will flow through the articles, and opens a valve 42 to the steam inlet, so that steam will flow into the vessel. The steam heats the air and water flowing through the articles, the water being heated by the steam condensing in it. The circulating air is mixed whith the steam and brings about an intense mixing and heating effect inside the chamber 24 on the water which is sprayed over the articles and flows downwards through them, so that all parts of the articles will be heated evenly and rapidly.

A temperature sensor 44 senses the temperatures in the chamber 24 and regulates via the steam valve 42 the steam supply to the vessel in dependence of the temperature in the chamber 24.

When another temperature sensor 46 located in a representative glass package in the chamber 24, senses that the desired treatment temperature has been reached in the package, it gives a signal to a timer 48 of the control means to start. When the timer has run the time, during which the desired heat treatment shall take place, it initiates simultaneous closing of the steam valve 42 and opening of the valves 50 and 52 of the heat exchangers 18 and 32, respectively, so that cooling water will flow through them and cool them both the water being sprayed over the articles and the gas mixture circulated through the articles. The circulating gas mixture brings about an intense mixing and cooling effect inside the chamber 24 on the water which is sprayed over the articles and flows downwards through them, so that all parts of the articles will be cooled evenly and rapidly.

When the articles are cooled to the desired temperature the pump 16 and the impeller 34 are stopped and the valves 50 and 52 are closed, after which the water is discharged through a valve 60 and the pressure in the vessel 10 is equalized against the surrounding atmosphere pressure by opening of a valve 54. The vessel can then be opened and the heat treated, e.g. sterilized, articles be taken out.

During the whole process the desired pressure in the vessel is controlled by supplying sterile compressed air through a valve 56 or by discharging gaseous medium through the valve 54.

Tests have been made which show the difference in result between the two said known methods and the method according to the invention. The chamber 24 in an arrangement according to the drawing was filled with glass packages 26. The temperatures T1, T2 and T3 were measured in three different packages.

The first known method described in the description was carried out on the packages. The impeller 34 was standing still while the pump 16 was running, spraying water over the packages. Heating was effected by steam only from the steam inlet 38. Cooling was effected by the heat exchanger 18 only. The result is evident from Table 1.

Without moving the packages in the chamber 24 the second known method described in the description was carried out on the packages. The pump 16 was standing still while the impeller 34 was running and circulated gaseous medium between the packages. Heating was effected by steam only from the steam inlet 38. Cooling was effected by the heat exchangers 32 only. The result is evident from Table 2.

The packages were furthermore subjected to the method according to the invention. The pump 16 as well as the impeller 34 were running. Heating was effected by steam only from the steam inlet 38. Cooling was effected by as well the heat exchanger 18 as by the heat exchangers 32. The result is evident from Table 3.

TABLE 1

| | Circulating water only | | | |
|---|---|---|---|---|
| | Time min., sec. | T1 °C. | T2 °C. | T3 °C. |
| Heating | 0'00" | 42,1 | 37,8 | 36,6 |
| | 2'00" | 84,9 | 90,4 | 84,7 |
| | 4'00" | 113,4 | 118,0 | 114,5 |
| | 6'00" | 127,5 | 128,7 | 127,9 |
| Sterilizing | 6'00" | 127,5 | 128,7 | 127,9 |
| | 7'00" | 127,8 | 127,9 | 127,8 |
| | 8'00" | 127,9 | 128,0 | 127,9 |
| Cooling | 8'00" | 127,9 | 128,0 | 127,9 |
| | 9'00" | 100,6 | 97,5 | 98,2 |
| | 10'00" | 76,1 | 74,2 | 74,2 |
| | 11'45" | 48,0 | 47,6 | 47,5 |

TABLE 2

| | Circulating gaseous medium only | | | |
|---|---|---|---|---|
| | Time min., sec. | T1 °C. | T2 °C. | T3 °C. |
| Heating | 0'00" | 36,0 | 28,7 | 35,8 |
| | 1'00" | 94,5 | 89,6 | 88,8 |
| | 2'00" | 123,1 | 121,9 | 119,6 |
| | 2'30" | 129,0 | 128,8 | 127,2 |
| Sterilizing | 2'30" | 129,0 | 128,8 | 127,2 |
| | 3'30" | 128,0 | 128,0 | 127,7 |
| | 4'30" | 128,1 | 128,0 | 127,9 |
| Cooling | 4'30" | 128,1 | 128,0 | 127,9 |
| | 5'30" | 90,4 | 89,0 | 99,3 |
| | 9'30" | 67,2 | 52,7 | 65,5 |
| | 13'15" | 49,5 | 34,5 | 45,7 |

TABLE 3

| | Both circulating water and circulating gaseous medium | | | |
|---|---|---|---|---|
| | Time min., sec. | T1 °C. | T2 °C. | T3 °C. |
| Heating | 0'00" | 37,5 | 35,0 | 36,4 |
| | 2'00" | 79,4 | 78,0 | 78,5 |
| | 4'00" | 110,5 | 110,0 | 109,8 |
| | 6'00" | 128,0 | 127,8 | 127,8 |
| Sterilizing | 6'00" | 128,0 | 127,8 | 127,8 |
| | 7'00" | 127,8 | 127,8 | 127,8 |
| | 8'00" | 127,8 | 127,8 | 127,8 |
| Cooling | 8'00" | 127,8 | 127,8 | 127,8 |
| | 9'00' | 100,2 | 97,0 | 98,1 |
| | 10'00" | 74,2 | 73,6 | 73,6 |
| | 11'30" | 48,9 | 49,2 | 49,2 |

From the above tables it is evident that the method and the arrangement according to the invention result in that the heat treatment of the articles takes place rapidly and simultaneously homogeneously, so that the articles at each moment during the treatment show an extraordinary even temperature distribution over the whole chamber 24. All the articles reach rapidly and simultaneously the desired treatment temperature during the heating without any part of the articles lagging in temperature respect, which would imply a harmful under-treatment of this part of the articles during the subsequent heat treatment. After that, all the articles keep at the desired treatment temperature without any part being neither colder nor warmer, which would be harmful to the treatment result. During the cooling the temperature of the articles sinks rapidly and simultaneously with the advantage that no part of the articles is staying at a higher temperature, which would imply a harmful over-treatment of the articles.

A cause contributing to the even temperature distribution during the heating is that the articles then are exposed to warm medium from two directions simultaneously, viz. partly by warm gas mixture which flows upwards through the articles from below and is cooled by the articles on its way upwards through the articles, and partly by warm water which flows downwards through the articles from above and is cooled by the articles on its way downwards through them.

A cause contributing to the even temperature distributing during the cooling is that the articles then are exposed to cold medium from two directions simultaneously, viz. partly by cold gas mixture, cooled by the heat exchangers 32, which gas mixture flows upwards through the articles from below and is heated by the articles on its way upwards through them and partly by cold water, cooled by the heat exchanger 18, which water flows downwards through the articles from above and is heated by the articles on its way downwards through the them.

Besides being applicable to sterilization the invention is also with advantage applicable to other kinds of heat treatments in order to kill micro-organisms, e.g. pasteurizing and tyndalizing.

I claim:

1. Method for heat treatment of articles (26) which are placed in a chamber (24) in a pressure vessel (10), heat being supplied to and heat being removed from, respectively, the articles (26) via water circulated in a closed circulation circuit (14,16,18, 20) and sprayed over the articles, which water during a heating period is heated by steam being introduced into the vessel and during a cooling period cooled by a first heat exchanger

(18) in the circulation circuit, characterized in that simultaneously as the water is sprayed over the articles and flows downwards through them gaseous medium in the vessel is forced to flow upwards through the articles.

2. Method according to claim 1, characterized in that during the cooling period the gaseous medium is brought to be cooled by a second heat exchanger (32).

3. Method according to claim 1 or 2, characterized in that the flows of water and gaseous medium are activated simultaneously during the heating period and a holding period at a treatment temperature as well as during the cooling period.

4. Arrangement for heat treatment of articles (26) which are placed in a chamber (24) in a pressure vessel for carrying out the method according to claim 1 and comprising a closed circulation circuit for water including a bottom outlet (14) in the pressure vessel, a pump (16), a first heat exchanger (18) and nozzles (20) which spray water over the articles in the chamber, and means (42) for supplying steam to the vessel, characterized in that an impeller (34) is arranged in the vessel for generating a forced circulating flow of gaseous medium through the articles (26) in countercurrent to the water flowing downwards through the articles (26) and that means (40) are arranged for driving the impeller (34) and the pump (16) simultaneously.

5. Arrangement according to claim 4, characterized in that a second heat exchanger (32) is arranged in the vessel (10) in the circulation path for cooling the gaseous medium during the cooling period.

6. Arrangement according to claim 5, characterized by a first means (40), which is arranged, on starting the heat treatment, simultaneously to start the pump (16), the impeller (34) and the steam supply, and a second means (46), arranged when a desired treatment temperature has been reached, to give a signal to a timer (48) to start, which timer (48) after a certain desired holding time at the treatment temperature is arranged to cut off the steam supply.

7. Arrangement according to claim 6, characterized in that the timer (48) is arranged, after said holding time, to initiate supply of cooling medium to the first (18) and the second (32) heat exchanger so that the water which is sprayed over the articles and the circulating gaseous medium, respectively, are cooled.

* * * * *